(12) United States Patent
Aida et al.

(10) Patent No.: US 8,247,626 B2
(45) Date of Patent: Aug. 21, 2012

(54) METHOD FOR PURIFYING TETRAFLUOROETHYLENE

(75) Inventors: Shigeru Aida, Tokyo (JP); Manabu Sato, Tokyo (JP); Takeya Sakamoto, Tokyo (JP); Nobuo Matsushita, Kitakyushu (JP); Yuuji Hayase, Kitakyushu (JP); Tomohiro Gotou, Kitakyushu (JP); Kenji Fujiwara, Kitakyushu (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 12/908,911

(22) Filed: Oct. 21, 2010

(65) Prior Publication Data

US 2011/0034740 A1 Feb. 10, 2011

Related U.S. Application Data

(63) Continuation of application No. PCT/JP09/056979, filed on Apr. 3, 2009.

(51) Int. Cl.
*C07C 21/00* (2006.01)
(52) U.S. Cl. .................. 570/189; 570/136; 570/179
(58) Field of Classification Search .................. None
See application file for complete search history.

(56) References Cited

U.S. PATENT DOCUMENTS

| | | | | |
|---|---|---|---|---|
| 2,457,970 A | * | 1/1949 | Bailie | 502/9 |
| 2,692,818 A | * | 10/1954 | Bewick | 423/500 |
| 2,737,533 A | | 3/1956 | Marks et al. | |
| 5,652,147 A | * | 7/1997 | Kawamura et al. | 436/142 |
| 6,495,257 B1 | * | 12/2002 | Terase et al. | 428/404 |

FOREIGN PATENT DOCUMENTS

| | | |
|---|---|---|
| JP | 03-223219 | 10/1991 |
| JP | 08-310979 | 11/1996 |
| JP | 2667542 | 6/1997 |
| JP | 09-313950 | 12/1997 |
| JP | 11-246447 | 9/1999 |
| JP | 2003-024776 | 1/2003 |
| JP | 3496219 | 11/2003 |
| WO | 95-08762 | 3/1995 |

OTHER PUBLICATIONS

International Search Report issued Jun. 10, 2009, in PCT/JP09/056979, filed Apr. 3, 2009.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

To provide a method for purifying tetrafluoroethylene by removing, from tetrafluoroethylene containing a polymerization inhibitor, the polymerization inhibitor by adsorption.

A method of bringing tetrafluoroethylene containing a polymerization inhibitor into contact with a silica gel containing a metal salt in an amount of from 250 to 100,000 mass ppm as calculated as metal atoms to remove the polymerization inhibitor by adsorption, and the metal salt is preferably a salt of a metal of Group 3 to 13 of the Periodic Table, more preferably a salt of a metal of Group 8 to 10 of the Periodic Table. For example, as the metal salt, a salt of at least one metal selected from the group consisting of iron, cobalt, nickel, ruthenium, rhodium, palladium, osmium, iridium and platinum may be used.

17 Claims, No Drawings

METHOD FOR PURIFYING TETRAFLUOROETHYLENE

This application is a continuation of PCT/JP09/056,979 filed Apr. 3, 2009. Priority to Japan 2008-115823 filed Apr. 28, 2008, is claimed.

TECHNICAL FIELD

The present invention relates to a method for purifying tetrafluoroethylene by removing a polymerization inhibitor added to the tetrafluoroethylene by adsorption.

BACKGROUND ART

Tetrafluoroethylene is a very useful compound as a raw material of fluoropolymers such as fluororesins and fluororubbers, and fluorinated solvents. However, tetrafluoroethylene (hereinafter sometimes referred to as TFE) has very high polymerizability, and if it is stored in a gaseous state or a liquid state, it undergoes polymerization, and it may decompose by the heat of polymerization and explode. Therefore, in general, for the purpose of suppressing the polymerization reaction, various polymerization inhibitors are added when TFE is stored (the following Patent Document 1). However, if a polymerization inhibitor remains in TFE, a desired polymerization reaction will not proceed, whereby no fluoropolymer can be obtained. Accordingly, the polymerization inhibitor is removed immediately before TFE is used for the polymerization reaction or the like, and then it is subjected to polymerization.

As a method of removing the polymerization inhibitor from TFE, a method of distillation, absorption by sulfuric acid, or adsorption by silica gel, zeolite, allophane or the like has been known (the following Patent Documents 2, 3 and 4). Particularly, a method of adsorbing the polymerization inhibitor by silica gel is industrially useful since it can be carried out easily at a low cost. However, it has such problems that TFE is polymerized in the interior of the silica gel particles as porous bodies to form a polymer, which clogs the pores of the silica gel, whereby the performance of the silica gel to adsorb the polymerization inhibitor will be decreased, the used silica gel is hardened by the polymer, whereby removal of the silica gel from a packed column will be difficult, if TFE is polymerized, TFE will decompose by the heat of polymerization, etc.

Patent Document 1: U.S. Pat. No. 2,737,533
Patent Document 2: Japanese Patent No. 2,667,542
Patent Document 3: JP-A-11-246447
Patent Document 4: Japanese Patent No. 3,496,219

DISCLOSURE OF THE INVENTION

Object to be Accomplished by the Invention

In order to solve the above problems, the present inventors have conducted extensive studies and as a result, accomplished the present invention. That is, it is an object of the present invention to provide a novel method for removing, from tetrafluoroethylene containing a polymerization inhibitor, the polymerization inhibitor by adsorption.

Means to Accomplish the Object

The present invention provides the following method for purifying tetrafluoroethylene.

[1] A method for purifying tetrafluoroethylene, which comprises bringing tetrafluoroethylene containing a polymerization inhibitor into contact with a silica gel containing a metal salt in an amount of from 250 to 100,000 mass ppm as calculated as metal atoms to remove the polymerization inhibitor by adsorption.

[2] The method for purifying tetrafluoroethylene according to the above [1], wherein the metal salt is a salt of a metal of Group 3 to 13 of the Periodic Table.

[3] The method for purifying tetrafluoroethylene according to the above [1], wherein the metal salt is a salt of a metal of Group 8 to 10 of the Periodic Table.

[4] The method for purifying tetrafluoroethylene according to the above [1], wherein the metal salt is a salt of at least one metal selected from the group consisting of iron, cobalt, nickel, ruthenium, rhodium, palladium, osmium, iridium and platinum.

[5] The method for purifying tetrafluoroethylene according to any one of the above [1] to [4], wherein the silica gel is produced by immersing a starting material silica gel in an aqueous solution in which the metal salt is dissolved.

[6] The method for purifying tetrafluoroethylene according to any one of the above [1] to [5], wherein the metal salt is an iron salt.

[7] The method for purifying tetrafluoroethylene according to the above [6], wherein the content of the iron salt in the silica gel is from 300 to 10,000 mass ppm as calculated as iron atoms.

[8] The method for purifying tetrafluoroethylene according to the above [6] or [7], wherein the silica gel further contains cobalt chloride in an amount of from 400 to 50,000 mass ppm as calculated as cobalt atoms.

[9] The method for purifying tetrafluoroethylene according to any one of the above [1] to [8], wherein the specific surface area of the silica gel is from 100 $m^2/g$ to 1,000 $m^2/g$.

[10] The method for purifying tetrafluoroethylene according to any one of the above [1] to [9], wherein the average particle size of the silica gel is from 0.1 mm to 10 mm.

[11] The method for purifying tetrafluoroethylene according to any one of the above [1] to [10], wherein the polymerization inhibitor is a terpene.

[12] The method for purifying tetrafluoroethylene according to any one of the above [1] to [11], wherein the temperature at which the tetrafluoroethylene containing the polymerization inhibitor and the silica gel are brought into contact with each other is from −20° C. to 20° C.

[13] The method for purifying tetrafluoroethylene according to any one of the above [1] to [12], wherein when the tetrafluoroethylene containing the polymerization inhibitor and the silica gel are brought into contact with each other, the linear velocity of the tetrafluoroethylene is from 0.005 m/sec to 1 m/sec.

Effects of the Invention

According to the method for purifying tetrafluoroethylene of the present invention, when a polymerization inhibitor is removed from TFE containing the polymerization inhibitor by adsorption by a silica gel, formation of a polymer in the interior of the silica gel particles can be prevented. Accordingly, problems such that the pores of the silica gel are clogged, whereby the performance of the silica gel to adsorb the polymerization inhibitor is decreased, can be suppressed. Further, problems such that the used silica gel is hardened by the polymer, whereby its removal from a packed column will be difficult, can be suppressed. Further, TFE will not decompose by the heat of polymerization of TFE.

The present invention is particularly useful as a method for purifying TFE, which comprises removing a polymerization inhibitor from a starting material TFE immediately before the reaction, in an industrial process for producing a fluoropolymer or a fluorinated solvent.

BEST MODE FOR CARRYING OUT THE INVENTION

The method for purifying tetrafluoroethylene of the present invention comprises bringing tetrafluoroethylene containing a polymerization inhibitor into contact with a silica gel containing a metal salt to remove the polymerization inhibitor by adsorption, whereby initiation of a polymerization reaction of TFE caused by the polymerization inhibitor being removed by adsorption by a silica gel at the time of purifying TFE, can be suppressed, and formation of a polymer in the interior of the silica gel particles can be suppressed.

In the present invention, the metal salt is preferably a salt of any metal of Group 3 to 10 of the Periodic Table, more preferably a salt of any metal of Group 8 to 10 of the Periodic Table. Specifically, it may be a salt of at least one metal selected from the group consisting of iron, cobalt, nickel, ruthenium, rhodium, palladium, osmium, iridium and platinum. Most preferred is an iron salt or a cobalt salt.

The acid to form the above metal salt is preferably an inorganic acid such as sulfuric acid, hydrochloric acid, nitric acid, phosphoric acid or carbonic acid, and is particularly preferably sulfuric acid or hydrochloric acid.

In the present invention, the content of the metal salt in the above silica gel is preferably from 250 to 100,000 mass ppm, preferably from 300 to 10,000 mass ppm, more preferably from 400 to 5,000 mass ppm as calculated as metal atoms. If the content is 250 mass ppm or less, no effect of suppressing the polymerization reaction will be obtained, and if it is 100,000 mass ppm or more, the cost of production of the silica gel will be high, or the metal salt may have an influence over the adsorption properties of the silica gel.

The silica gel containing the above metal salt may be obtained e.g. by a method of adding a metal salt containing metal atoms to the starting material for production of the silica gel, or a method of immersing the starting material silica gel prepared into a form of particles in an aqueous solution in which the metal salt is dissolved to impregnate the silica gel particles with the metal salt, but the production method is not limited thereto. Among the above methods, the method of immersing the starting material silica gel in an aqueous solution in which the metal salt is dissolved to impregnate the silica gel particles with the metal salt, which is easily carried out, is preferred.

Further, it is preferred to incorporate water in the starting material silica gel before the starting material silica gel in the form of particles is immersed in the aqueous solution, whereby fracture of the starting material silica gel in the form of particles when immersed can be prevented. In a case where water is incorporated in the starting material silica gel before it is immersed in the aqueous solution, the water content of the starting material silica gel is preferably from 20 mass % to 35 mass %, more preferably from 28 mass % to 32 mass %.

In the present invention, a silica gel containing at least two types of metal salts in combination may also be used.

In the present invention, the specific surface area of the silica gel is preferably from 100 $m^2/g$ to 1,000 $m^2/g$, more preferably from 300 $m^2/g$ to 800 $m^2/g$, most preferably from 500 $m^2/g$ to 700 $m^2/g$. If the specific surface area of the silica gel is smaller than 100 $m^2/g$, the amount of the polymerization inhibitor which is adsorbed per unit mass of the silica gel will be decreased, and if the specific surface area of the silica gel is intended to be larger than 1,000 $m^2/g$, the process for producing such a silica gel will be complicated, and the cost of production of the silica gel will be high. The specific surface area of the silica gel is preferably within the above range, whereby there are no such problems.

In the present invention, the silica gel is preferably used as packed in an adsorption column. Further, it is preferably in the form of particles, whereby it is easily handled when packed in an adsorption column or removed from the adsorption column. The average particle size of the silica gel particles is preferably from 0.1 mm to 10 mm, more preferably from 0.5 mm to 5 mm, most preferably from 1 mm to 4 mm. If the average particle size of the silica gel is smaller than 0.1 mm, the pressure loss when it is brought into contact with TFE containing the polymerization inhibitor will be great, whereby it will be difficult to increase the rate of purifying TFE. Further, if the average particle size of the silica gel is larger than 10 mm, the packing density when the silica gel particles are packed in the adsorption column will be decreased, whereby the efficiency in adsorption of the polymerization inhibitor will be decreased. The average particle size of the silica gel is preferably within the above range, whereby there are no such problems.

In the present invention, the water content of the silica gel is preferably from 0.01 mass % to 10 mass %, more preferably from 0.1 mass % to 5 mass %, most preferably from 0.2 mass % to 2 mass %. If the water content of the silica gel is intended to be lower than 0.01 mass %, the silica gel drying step, or its storage or handling method will be complicated. If the water content is higher than 10 mass %, water may be included in the TFE with which the silica gel is brought into contact, or the performance to adsorb the polymerization inhibitor will be decreased. The water content of the silica gel is preferably within the above range, whereby there are no such problems.

In the most preferred embodiment of the present invention, the above metal salt is an iron salt. In a case where an iron salt is used, the content of the iron salt in the silica gel is preferably from 250 to 100,000 mass ppm, more preferably from 300 to 10,000 mass ppm, most preferably from 400 to 5,000 mass ppm, as calculated as iron atoms, based on the mass of the silica gel. If the iron atom content in the silica gel is lower than 250 mass ppm, TFE may be polymerized in the interior of the silica gel particles to form a polymer, and TFE will decompose by the heat of polymerization of TFE, the pores of the silica gel may be clogged, thereby to decrease the performance to adsorb the polymerization inhibitor, or the used silica gel is hardened by the polymer, whereby its removal will be difficult. Further, if the iron atom content in the silica gel is higher than 100,000 mass ppm, the silica gel contains iron atoms more than necessary, whereby the cost of production of the silica gel will be high. Further, the properties to adsorb the polymerization inhibitor will be decreased. The iron atom content of the silica gel is preferably within the above range, whereby there are no such problems.

The above iron salt is preferably ferrous sulfate, ferric sulfate, ferrous chloride, ferric chloride, ferrous nitrate or ferric nitrate, more preferably ferrous sulfate or ferric sulfate.

The silica gel containing the metal salt in the present invention also preferably contains, in addition to the above metal salt such as an iron salt, a cobalt salt such as cobalt(II) chloride ($CoCl_2$). A silica gel containing cobalt chloride undergoes discoloration by a change in the water content of the silica gel, and accordingly the water content of the silica gel can be visually evaluated. For example, when the silica gel has a water content of at most 20%, it is blue, and if its water content exceeds 40%, it will turn red. The content of cobalt chloride is preferably from 400 to 50,000 mass ppm, more preferably from 1,000 to 30,000 mass ppm, most preferably from 2,000 to 15,000 mass ppm, as cobalt atoms. If the content of cobalt chloride is lower than 400 mass ppm, it will be difficult to visually determine the color. Further, if the content of cobalt chloride is higher than 50,000 mass ppm, cobalt chloride is contained more than necessary, whereby the cost of production of the silica gel will be high. Further, the properties to adsorb the polymerization inhibitor will be decreased. The cobalt chloride content in the silica gel is preferably within the above range, whereby there are no such problems.

Further, as shown in after-mentioned Examples, a cobalt salt also has an effect of suppressing the polymerization reaction of TFE, whereby additive and synergistic effects with other metal salt can be expected.

As a method of impregnating the silica gel with cobalt chloride, preferred is a method of immersing a silica gel containing a metal salt such as an iron salt in an aqueous solution of cobalt chloride to impregnate the silica gel particles with cobalt chloride. Further, preferred is a method of immersing the starting material silica gel prepared into a form of particles in an aqueous solution containing a metal salt such as an iron salt and cobalt chloride. The latter method is more preferred, since the starting material silica gel can be impregnated with cobalt chloride and other metal salt such as an iron salt at the same time, whereby the silica gel can easily be produced.

The polymerization inhibitor in the present invention is preferably a terpene compound such as α-pinene, β-pinene, α-terpinene, γ-terpinene, diterpene, terpinolene, isoterpinolene, camphene, p-cymene or p-menthane, more preferably α-pinene. Further, the amount of addition of the polymerization inhibitor to TFE is preferably from 10 to 1,000 mass ppm, more preferably from 20 to 500 mass ppm. If the amount of addition of the polymerization inhibitor in TFE is less than 10 mass ppm, polymerization of TFE cannot sufficiently be suppressed, and if it is larger than 1,000 mass ppm, removal will be difficult.

The content of the polymerization inhibitor in TFE purified by the method for purifying TFE of the present invention is preferably less than 1 mass ppm. If the content of the polymerization inhibitor in the purified TFE is 1 mass ppm or more, a large amount of a polymerization initiator will be required, and in addition, the polymerization reaction rate of TFE will be low, thus lowering the productivity of a polymer. Further, the polymerization inhibitor may be included in a polymer product, thus leading to drawbacks such as coloring in some cases.

As the method for purifying TFE of the present invention, preferred is a method of packing a silica gel containing a specific amount of a metal salt in an adsorption column, and introducing TFE containing a polymerization inhibitor to the adsorption column to bring it into contact with the silica gel thereby to remove the polymerization inhibitor by adsorption. The temperature at which TFE and the silica gel are brought into contact with each other in the adsorption column is preferably from −20° C. to 20° C., more preferably from 0° C. to 15° C. If the contact temperature is lower than −20° C., the high pressure TFE will be liquefied, such being unfavorable, and if the contact temperature is higher than 20° C., a polymer of TFE is likely to form, such being unfavorable. Further, the rate at to which TFE containing the polymerization inhibitor is made to flow through the adsorption column is such that the linear velocity of TFE which pass through the column is preferably from 0.005 m/sec to 1 m/sec, more preferably from 0.01 m/sec to 0.5 m/sec, most preferably from 0.02 m/sec to 0.1 m/sec. If the linear velocity of TFE is lower than 0.005 m/sec, the TFE purification rate will be low, thus lowering the productivity. If the linear velocity of TFE is higher than 1 m/sec, adsorption of the polymerization inhibitor may not sufficiently be carried out.

EXAMPLES

Now, the present invention will be described in further detail with reference to Examples. However, it should be understood that the present invention is by no means restricted to such specific Examples. Physical properties such as the iron atom content were evaluated by the following methods.

[Iron Atom and Cobalt Atom Content (Unit: Mass Ppm)]

The silica gel was dissolved in an acidic aqueous solution, and the aqueous solution in which the silica gel was dissolved was subjected to analysis by an inductively-coupled plasma emission spectrometry ICP (manufactured by Hitachi, Ltd., P-4000) to measure the concentrations of iron atoms and cobalt atoms contained in the above aqueous solution to quantitatively determine the iron atoms and the cobalt atoms contained in the silica gel.

[Specific Surface Area (Unit: $m^2/g$)]

Using BELSORP 28 manufactured by BEL Japan, Inc., using a nitrogen gas, the BET specific surface area of the silica gel was measured.

[Average Particle Size (Unit: mm)]

Measured in accordance with a method disclosed in JIS Z 0701 using JIS standard sieves with mesh size of 4.00 mm, 3.35 mm, 2.80 mm, 2.36 mm, 1.70 mm and 0.85 mm.

[Water Content (Unit: Mass %)]

Measured in accordance with a method disclosed in JIS Z0701.

[Content (Unit: Mass Ppm) of Polymerization Inhibitor (α-Pinene) in TFE]

Analyzed by gas chromatography equipped with a hydrogen flame ionization detector.

Comparative Example 1

4.5 g of silica gel 1 manufactured by AGC Si-Tech Co., Ltd. (Hishi-pearl white, specific surface area: 595 $m^2/g$, average particle size: 2.70 mm, iron atom content: 14 ppm, cobalt: undetected) was packed in a tubular pressure vessel having an inner diameter of 8 mm and a length of 100 mm. Then, the vessel was immersed in ice water, and vacuuming and nitrogen pressurization were repeated three times to remove the air in the vessel, and then TFE was purged to replace the nitrogen gas in the vessel with TFE. Then, TFE was slowly introduced until the pressure became 1.5 MPaG, and the vessel was left to stand for 24 hours. Then, TFE was purged, and the state of the silica gel in the interior was confirmed, whereupon all the particles of the silica gel 1 which had been transparent and colorless turned opaque white, and formation of a polymer of TFE in the interior of the silica gel particles was suggested.

Example 1

While 15 kg of silica gel used in Comparative Example 1 was stirred by a mixer, an aqueous solution having 11.2 g of ferrous sulfate heptahydrate dissolved in 15 kg of demineralized water was sprayed until the water content of the silica gel became 7 mass %. Then, the above silica gel was immersed in the above ferrous sulfate aqueous solution and left to stand for 72 hours. Then, the silica gel was drawn from the aqueous solution using a stainless steel mesh and left to stand on the mesh for 16 hours to separate the silica gel from the aqueous solution. The obtained silica gel was dried in an oven at 150° C. for 6 hours to obtain silica gel 2 containing 540 mass ppm of iron atoms. Then, this silica gel 2 was brought into contact with TFE in the same manner as in Comparative Example 1, whereupon silica gel 2 maintained transparency, and no polymer of TFE was formed.

Example 2

15 kg of silica gel 1 used in Comparative Example 1 was put in a mixer, and water mist was sprayed for about 6 hours with stirring to make the silica gel contain water until the water content became 30 mass %. The silica gel containing water was immersed in an aqueous solution having 9 kg of cobalt(II) chloride hexahydrate dissolved in 90 kg of demineralized water to impregnate the silica gel with cobalt chloride with stirring. 72 hours later, the silica gel was drawn from the aqueous solution using a stainless steel mesh and left to stand on the mesh for 16 hours to separate the silica gel from the aqueous solution. The obtained silica gel was dried in an oven at 150° C. for 6 hours to obtain silica gel 3 containing 3,300 mass ppm of cobalt atoms. This silica gel 3 was brought into contact with TFE in the same manner as in Comparative Example 1, whereupon transparency of a small portion of the particles of silica gel 3 was decreased, and formation of a polymer of TFE was suggested, but the amount of the polymer formed was smaller than in Comparative Example 1.

Preparation Example 1

30 kg of silica gel 1 used in Comparative Example 1 was put in a mixer, and water mist was sprayed for about 6 hours with stirring to make the silica gel 1 contain water until the water content became 30 mass ppm. Then, the silica gel containing water was immersed in an aqueous solution having ferrous sulfate heptahydrate in an amount as identified in the following Table 1 and 9 kg of cobalt(II) chloride hexahydrate dissolved in 90 kg of demineralized water, to impregnate the silica gel with iron sulfate and cobalt chloride with stirring. 72 hours later, the silica gel was drawn from the aqueous solution by a stainless steel mesh and left to stand on the mesh for 16 hours to separate the silica gel from the aqueous solution. The obtained silica gel was dried in an oven at 150° C. for 6 hours to obtain each of silica gels 4 to 8.

TABLE 1

| Silica gel | Ferrous sulfate heptahydrate (g) |
|---|---|
| 4 | 765 |
| 5 | 765 |
| 6 | 898 |
| 7 | 1,162 |
| 8 | 961 |

Physical properties such as the iron atom content of each of silica gels 4 to 8 are shown in the following Table 2.

TABLE 2

| Silica gel | Iron atom content (ppm) | Cobalt atom content (ppm) | Average particle size (mm) | Specific surface area (m²/g) | Water content (mass %) |
|---|---|---|---|---|---|
| 4 | 416 | 4,500 | 2.74 | 557 | 0.53 |
| 5 | 453 | 4,400 | 2.67 | 571 | 0.51 |
| 6 | 510 | 4,200 | 2.70 | 564 | 0.50 |

TABLE 2-continued

| Silica gel | Iron atom content (ppm) | Cobalt atom content (ppm) | Average particle size (mm) | Specific surface area (m²/g) | Water content (mass %) |
|---|---|---|---|---|---|
| 7 | 595 | 4,100 | 2.67 | 580 | 0.47 |
| 8 | 502 | 4,300 | 2.69 | 575 | 0.45 |

Preparation Example 2

Silica gels 9 to 13 were prepared in the same manner as in Preparation Example 1 except that no ferrous sulfate heptahydrate was added to the aqueous solution in which the silica gel was immersed. Physical properties such as the iron atom content are shown in the following Table 3.

TABLE 3

| Silica gel | Iron atom content (ppm) | Cobalt atom content (ppm) | Average particle size (mm) | Specific surface area (m²/g) | Water content (mass %) |
|---|---|---|---|---|---|
| 9 | 13 | 3,400 | 2.57 | 576 | 0.62 |
| 10 | 14 | 3,500 | 2.73 | 581 | 0.64 |
| 11 | 17 | 3,800 | 2.64 | 577 | 0.58 |
| 12 | 18 | 3,500 | 2.57 | 552 | 1.7 |
| 13 | 22 | 3,700 | 2.64 | 581 | 0.57 |

Example 3

In tubes of a tubular heat exchanger (inner diameter of the main body: 750 mm, having 110 tubes with an inner diameter of 42 mm and a length of 1,200 mm in the interior of the main body), 30 kg each of silica gels 4 to 8 (150 kg in total) were packed, and vacuuming and nitrogen pressurization were repeated three times to replace the atmosphere in the interior of the tubular heat exchanger with nitrogen. Then, while water of 10° C. was made to flow around the tubes in which silica gels were packed for cooling, TFE containing 150 mass ppm of α-pinene was slowly introduced to replace the nitrogen gas in the tubes with TFE. Then, TFE containing 150 mass ppm of α-pinene was brought into contact with silica gels under an elevated pressure of 1.5 MPaG at a linear velocity of 0.037 m/sec to remove α-pinene. From the results of analysis of the purified TFE, no α-pinene was detected. Then, after 38 tons of TFE was continuously treated, the state of silica gels was confirmed. As a result, no polymer of TFE was formed with respect to any of silica gels 4 to 8, and silica gels could easily be removed from the tubes by suction.

Example 4

Purification of TFE was carried out in the same manner as in Example 3 except that the silica gels used were changed to silica gels 9 to 13. In treatment of 38 tons, no α-pinene was detected in the purified TFE, and accordingly silica gels 9 to 13 were found to be excellent in the TFE purification properties. However, as a result of confirmation of the state of silica gels after used for purification of TFE, a polymer of TFE was formed in every silica gel, and the silica gels could not easily be drawn from the tubes, and it was found that the effect of suppressing polymerization of TFE is not sufficient as compared with silica gels 4 to 8 used in Example 3.

The results in Examples 3 to 4 are summarized as follows. As shown in Example 4, by the silica gel containing a cobalt salt, polymerization reaction of TFE caused by α-pinene being adsorbed in the silica gel and removed, was suppressed, and 38 tons could be treated. However, after 38 tons of TFE was continuously treated, a polymer of TFE was accumulated, and it was very difficult to draw the silica gels. On the other hand, as shown in Example 3, when the silica gel contains an iron salt and a cobalt salt, a more excellent effect of suppressing polymerization could be obtained, a polymer of TFE was not accumulated even when 38 tons of TFE was continuously treated, and no hardening of the silica gel by the polymer occurred. Accordingly, both cobalt atoms and iron atoms provide excellent effect of suppressing polymerization, but more excellent effect of suppressing polymerization by iron atoms was confined.

Example 5

125 g of silica gel 4 used in Example 3 was packed in a tubular pressure vessel having an inner diameter of 27 mm and a length of 300 mm. Then, the vessel was immersed in ice water, and vacuuming and nitrogen pressurization were repeated three times to remove the air in the vessel, and then TFE was purged to replace the nitrogen gas in the vessel with TFE. Then, TFE was slowly introduced until the pressure became 1.5 MPaG, and the vessel was left to stand for 24 hours. Then, TFE was purged, and the state of silica gel 4 in the interior was confirmed, whereupon no change in transparency and outer appearance was observed, and no formation of a polymer of TFE was confirmed.

Example 6

30 kg of silica gel 1 used in Comparative Example 1 was put in a mixer, and water mist was sprayed for about 6 hours with stirring to make the silica gel contain water until the water content became 30 mass %. Then, the silica gel containing water was immersed in an aqueous solution having 173 g of ferrous sulfate heptahydrate and 9 kg of cobalt(II) chloride hexahydrate dissolved in 90 kg of demineralized water to impregnate the silica gel with cobalt chloride with stirring. 72 hours later, the silica gel was drawn from the aqueous solution by a stainless steel mesh and left to stand on the mesh for 16 hours to separate the silica gel from the aqueous solution, thereby to obtain silica gel 14 containing 160 mass ppm of iron atoms and 4,700 mass ppm of cobalt atoms. The obtained silica gel 14 was brought into contact with TFE in the same mariner as in Example 5 and as a result, a part of particles became clouded, and formation of a polymer of TFE in the interior of the silica gel particles was confirmed.

INDUSTRIAL APPLICABILITY

According to the method for purifying TFE of the present invention, it is possible to easily remove a polymerization inhibitor in TFE. Accordingly, it is useful as a method for purifying TFE by removing a polymerization inhibitor from TFE by adsorption immediately before the reaction, in a process for producing a fluoropolymer or a fluorinated solvent. Further, it is particularly useful as an industrial purification method for removing a terpene which is a polymerization inhibitor from a highly reactive fluoromonomer as well as from TFE.

The entire disclosure of Japanese Patent Application No. 2008-115823 filed on Apr. 25, 2008 including specification, claims and summary is incorporated herein by reference in its entirety.

What is claimed is:

1. A method for purifying tetrafluoroethylene, which comprises bringing tetrafluoroethylene comprising a polymerization inhibitor into contact with a silica gel comprising a metal salt in an amount of from 250 to 100,000 mass ppm as calculated as metal atoms to remove the polymerization inhibitor by adsorption,
    wherein the metal salt is a salt of at least one metal selected from the group consisting of iron, cobalt, nickel, ruthenium, rhodium, palladium, osmium, iridium and platinum, and
    wherein the polymerization inhibitor is a terpene.

2. The method for purifying tetrafluoroethylene according to claim 1, wherein the metal salt is a salt of at least one metal selected from the group consisting of iron and cobalt.

3. The method for purifying tetrafluoroethylene according to claim 1, wherein the silica gel is produced by immersing a starting material silica gel in an aqueous solution in which the metal salt is dissolved.

4. The method for purifying tetrafluoroethylene according to claim 1, wherein the metal salt is an iron salt.

5. The method for purifying tetrafluoroethylene according to claim 4, wherein the content of the iron salt in the silica gel is from 300 to 10,000 mass ppm as calculated as iron atoms.

6. The method for purifying tetrafluoroethylene according to claim 4, wherein the silica gel further comprises cobalt chloride in an amount of from 400 to 50,000 mass ppm as calculated as cobalt atoms.

7. The method for purifying tetrafluoroethylene according to claim 1, wherein the specific surface area of the silica gel is from 100 $m^2/g$ to 1,000 $m^2/g$.

8. The method for purifying tetrafluoroethylene according to claim 1, wherein the average particle size of the silica gel is from 0.1 mm to 10 mm.

9. The method for purifying tetrafluoroethylene according to claim 1, wherein the temperature at which the tetrafluoroethylene comprising the polymerization inhibitor and the silica gel are brought into contact with each other is from −20° C. to 20° C.

10. The method for purifying tetrafluoroethylene according to claim 1, wherein when the tetrafluoroethylene comprising the polymerization inhibitor and the silica gel are brought into contact with each other, the linear velocity of the tetrafluoroethylene is from 0.005 m/sec to 1 m/sec.

11. The method for purifying tetrafluoroethylene according to claim 1, wherein the content of the metal salt in the silica gel is from 300 to 10,000 mass ppm as calculated as metal atoms.

12. The method for purifying tetrafluoroethylene according to claim 1, wherein the content of the metal salt in the silica gel is from 400 to 5,000 mass ppm as calculated as metal atoms.

13. The method for purifying tetrafluoroethylene according to claim 4, wherein the specific surface area of the silica gel is 100 $m^2/g$ to 1,000 $m^2/g$.

14. The method for purifying tetrafluoroethylene according to claim 4, wherein the silica gel is in the form of particles, the average particle size of the silica gel being 0.1 mm to 10 mm.

15. The method for purifying tetrafluoroethylene according to claim 1, wherein the content of the polymerization inhibitor in said tetrafluoroethylene prior to contact with said silica gel is 10 to 1,000 mass ppm, and wherein the content of the polymerization inhibitor in said tetrafluoroethylene after contact with said silica gel is less than 1 mass ppm.

16. The method for purifying tetrafluoroethylene according to claim 4, wherein the iron salt is ferrous sulfate, ferric sulfate, ferrous chloride, ferric chloride, ferrous nitrate or ferric nitrate.

17. The method for purifying tetrafluoroethylene according to claim 4, wherein the content of the polymerization inhibitor in said tetrafluoroethylene prior to contact with said silica gel is 10 to 1,000 mass ppm, and wherein the content of the polymerization inhibitor in said tetrafluoroethylene after contact with said silica gel is less than 1 mass ppm.

* * * * *

UNITED STATES PATENT AND TRADEMARK OFFICE
CERTIFICATE OF CORRECTION

| | |
|---|---|
| PATENT NO. | : 8,247,626 B2 |
| APPLICATION NO. | : 12/908911 |
| DATED | : August 21, 2012 |
| INVENTOR(S) | : Shigeru Aida et al. |

It is certified that error appears in the above-identified patent and that said Letters Patent is hereby corrected as shown below:

On the title page, Item (30), the Foreign Application Priority Data is omitted. Item (30) should read:

-- (30)       Foreign Application Priority Data

Apr. 25, 2008 (JP).............................. 2008-115823 --

Signed and Sealed this
Second Day of October, 2012

David J. Kappos
*Director of the United States Patent and Trademark Office*